United States Patent
Vogelbaum

(10) Patent No.: US 11,376,396 B2
(45) Date of Patent: Jul. 5, 2022

(54) CATHETER ASSEMBLY

(71) Applicant: THE CLEVELAND CLINIC FOUNDATION, Cleveland, OH (US)

(72) Inventor: Michael A. Vogelbaum, Moreland Hills, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 576 days.

(21) Appl. No.: 16/095,497

(22) PCT Filed: Apr. 20, 2017

(86) PCT No.: PCT/US2017/028530
§ 371 (c)(1),
(2) Date: Oct. 22, 2018

(87) PCT Pub. No.: WO2017/184820
PCT Pub. Date: Oct. 26, 2017

(65) Prior Publication Data
US 2019/0126007 A1    May 2, 2019

Related U.S. Application Data

(60) Provisional application No. 62/324,943, filed on Apr. 20, 2016.

(51) Int. Cl.
*A61M 25/00* (2006.01)
*A61M 25/01* (2006.01)

(52) U.S. Cl.
CPC .... *A61M 25/0026* (2013.01); *A61M 25/0102* (2013.01); *A61M 2025/0035* (2013.01);
(Continued)

(58) Field of Classification Search
CPC .......... A61M 25/0026; A61M 25/0102; A61M 2025/0035; A61M 2025/0037; A61M 25/003; A61M 2025/0025
See application file for complete search history.

(56) References Cited

U.S. PATENT DOCUMENTS 5,024,659 A    6/1991 Sjostrom
5,025,778 A    6/1991 Silverstein et al.
(Continued)

OTHER PUBLICATIONS

PCT International Search Report and Written Opinion for corresponding International Application Serial No. PCT/US2017/028530, dated Jul. 5, 2017, pp. 1-12.

*Primary Examiner* — Bhisma Mehta
*Assistant Examiner* — John J Crawford
(74) *Attorney, Agent, or Firm* — Tarolli, Sundheim, Covell & Tummino LLP

(57) ABSTRACT

A catheter assembly 10 comprises a catheter 12 including a longitudinally extending wall 16 with inner and outer surfaces. The inner surface of the wall defines a bore 22 extending longitudinally through the catheter defining a first lumen 52 and a second lumen 54. At least one of the first and second lumens communicates with an opening in the outer surface of the wall at a distal end of the catheter. An elongated separator 14 includes a longitudinally extending surface that at least partially defines the second lumen. The longitudinally extending surface of the separator is disposed asymmetrically relative to the bore when viewed in cross-section taken transverse to the longitudinal extent of the separator adjacent to a distal end of the separator. At least a portion of the separator is movable relative to the bore and the inner surface of the catheter wall.

13 Claims, 2 Drawing Sheets

(52) U.S. Cl.
CPC ............... *A61M 2025/0037* (2013.01); *A61M 2025/0079* (2013.01)

(56) References Cited

U.S. PATENT DOCUMENTS

| | | | | |
|---|---|---|---|---|
| 5,772,642 | A | * | 6/1998 | Ciamacco, Jr ....... A61N 5/1002 604/264 |
| 5,810,776 | A | | 9/1998 | Bacich et al. |
| 5,857,956 | A | * | 1/1999 | Liprie .................. A61N 5/1002 600/7 |
| 6,312,374 | B1 | * | 11/2001 | von Hoffmann ... A61M 25/104 600/3 |
| 6,450,937 | B1 | * | 9/2002 | Mercereau ........... A61N 5/1007 600/7 |
| 2002/0103472 | A1 | * | 8/2002 | Kramer ............. A61M 25/0023 604/507 |
| 2012/0041394 | A1 | | 2/2012 | Haider et al. |

* cited by examiner

CATHETER ASSEMBLY

RELATED APPLICATION

This application is a national phase application of and claims priority from PCT International Patent Application PCT/US2017/028,830, filed Aril 20, 2017, which claims priority from U.S. Provisional Patent Application Ser. No. 62/324,943, filed 20 Apr. 2016 and entitled CATHETER ASSEMBLY. The subject matter of each of the aforementioned applications is hereby incorporated by reference in its entirety.

FIELD OF THE INVENTION

The present invention relates to a catheter assembly that has two lumens and, more particularly, to a catheter assembly in which (a) a catheter wall defines a longitudinally extending bore and (b) a movable separator partially defines at least one of the two lumens in the bore.

BACKGROUND OF THE INVENTION

Convection enhanced delivery ("CED") of a bioactive agent involves introducing a fluid containing the bioactive agent into a patient's tissue under pressure so that the fluid moves through the tissue via bulk flow. Implementing CED generally involves inserting catheters into the tissue to be treated, such as cerebral tissue. To reduce the risk of hemorrhage and/or trauma to the tissue, it is desirable for such a catheter to have a small outside diameter. It is also desirable to prevent the introduction of air into the tissue prior to the fluid reaching the tissue, which will help prevent backflow of fluid along the outside of the catheter.

SUMMARY OF THE INVENTION

The present invention is directed to a catheter assembly that has two lumens and, more particularly, to a catheter assembly in which (a) a catheter wall defines a longitudinally extending bore and (b) a movable separator partially defines at least one of the two lumens in the bore.

In accordance with an embodiment of the present invention, a catheter assembly comprises a catheter including a longitudinally extending wall with an inner surface and an outer surface. The inner surface of the wall defines (a) a bore extending longitudinally through the catheter and (b) at least partially defines a first lumen in the bore and a laterally adjacent second lumen in the bore. At least one of the first lumen and the second lumen communicates with an opening in the outer surface of the wall adjacent a distal end of the catheter. An elongated separator includes a longitudinally extending surface that at least partially defines the second lumen. The longitudinally extending surface of the separator is disposed asymmetrically relative to the bore when viewed in cross-section taken transverse to the longitudinal extent of the separator adjacent to a distal end of the separator. At least a portion of the separator is movable relative to the bore and the inner surface of the wall of the catheter.

In accordance with another embodiment of the present invention, a catheter assembly comprises a catheter including a longitudinally extending wall with an inner surface and an outer surface. The inner surface of the wall (a) defines a bore extending longitudinally through the catheter and (b) at least partially defines a first lumen in the bore and a laterally adjacent second lumen in the bore. The second lumen communicates with an opening in the outer surface of the wall adjacent a distal end of the catheter. A flexible membrane extends longitudinally through the bore. The membrane includes a first major side surface presented toward the second lumen and an opposite second major side surface presented toward the first lumen. The membrane is attached to the wall of the catheter adjacent opposed edges of the first major side surface throughout a majority of the longitudinal extent of the membrane so as to separate the bore into the first lumen and the second lumen. The membrane extends transversely of the bore and is attached to the wall along a distal end of the membrane so as to close a distal end of the first lumen. At least a portion of the membrane is movable relative to the bore and the inner surface of the wall of the catheter.

In accordance with yet another embodiment of the present invention, a catheter assembly comprises a catheter including a longitudinally extending wall with an inner surface and an outer surface. The inner surface of the wall when viewed in cross-section taken transverse to the longitudinal extent of the wall is configured as an asymmetric closed geometric figure surrounding and defining a bore extending longitudinally through the catheter. A first portion of the inner surface of the wall and the asymmetric closed geometric figure at least partially define a first lumen in the bore. A second portion of the inner surface of the wall and the asymmetric closed geometric figure at least partially define a second lumen in the bore. The second lumen is laterally adjacent the first lumen. At least one of the first lumen and the second lumen communicates with an opening in the outer surface of the wall adjacent a distal end of the catheter. The catheter assembly also comprises a stylet with a longitudinally extending outer peripheral surface. A first portion of the outer peripheral surface of the stylet when viewed in cross-section taken transverse to the longitudinal extent of the outer peripheral surface closely conforms to the first portion of the inner surface of the wall and the closed geometric figure so that the stylet fits closely within the first lumen so as to occlude the first lumen when the stylet is received in the bore. A second portion of the outer peripheral surface of the stylet when viewed in cross-section taken transverse to the longitudinal extent of the outer peripheral surface is dissimilar to the second portion of the inner surface of the wall and the closed geometric figure so that the second portion of the outer peripheral surface of the stylet leaves open and partially defines the second lumen in the bore when the stylet is received in the bore.

BRIEF DESCRIPTION OF THE DRAWINGS

The foregoing and other features and advantages of the present invention will become apparent to one skilled in the art upon consideration of the following description of the invention and the accompanying drawings, in which.

DETAILED DESCRIPTION

FIGS. 1 through 5 illustrate a catheter assembly 10, in accordance with an example of the present invention. The catheter assembly 10 includes a catheter 12. The catheter 12 is made of a flexible biocompatible material, such as a medical grade silicone. As used in this application, "flexible" means that a material, such as the material of which the catheter 12 is made, is capable of being flexed, which is to say capable of being turned, bowed, or twisted without breaking. The catheter 12 may alternatively be made of a flexible and resilient biocompatible material, such as a medical grade silicone elastomer. As used in this application, "resilient" means that a material, such as the material of which the catheter 12 may alternatively be made, is capable of returning freely to a previous position, shape or condition, which is to say capable of recovering its size and shape after deformation.

Figure 3:
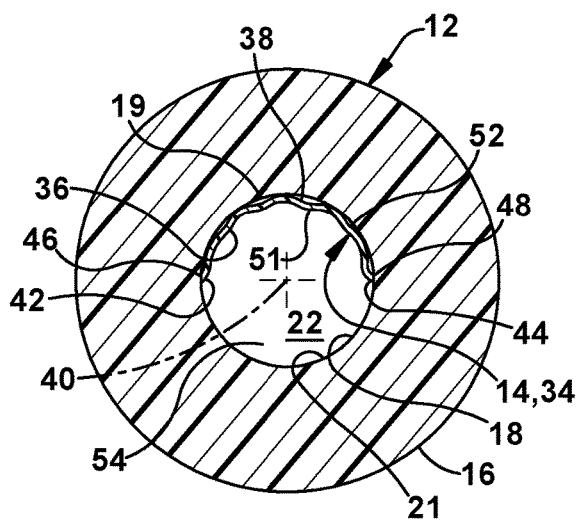
FIG. 3 is an enlarged transverse sectional view of the catheter assembly of FIG. 1 taken along view line 3-3 of FIG. 1.
Figure 4:
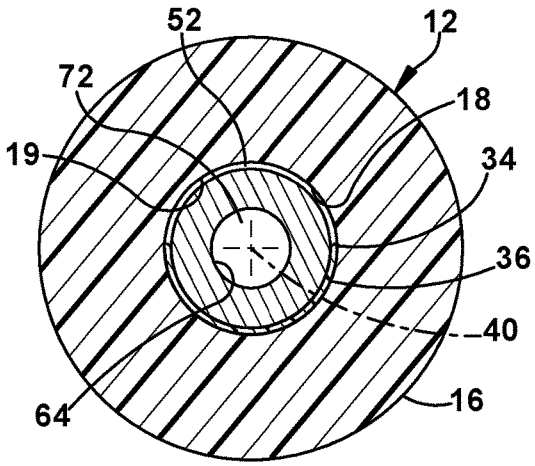
FIG. 4 is an enlarged transverse sectional view of the catheter assembly of FIG. 1 taken along view line 4-4 of FIG. 2.
Figure 5:
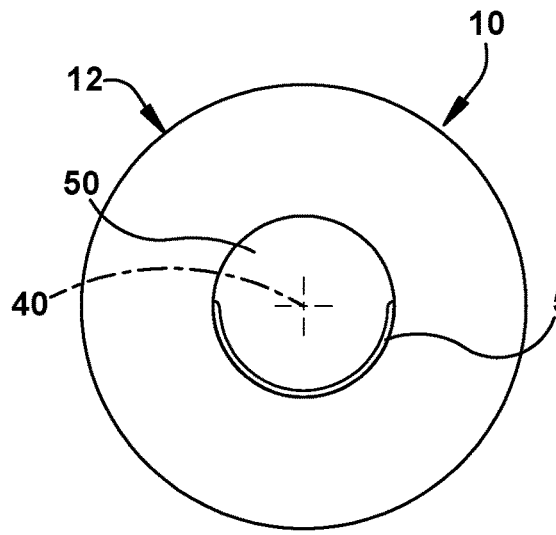
FIG. 5 is an end view of the catheter assembly of FIG. 1 taken along view line 5-5 of FIG. 2.

The catheter 12 includes a longitudinally extending, tubular wall 16. The wall 16 includes a radially inner surface 18 and a radially outer surface 20, which is presented in a direction away from or opposite the inner surface. Both the inner surface 18 and the outer surface 20 extend substantially the entire length of the catheter 12 from a proximal end 24 of the catheter to an opposite distal end 26 of the catheter. As shown in FIGS. 3 and 4, the inner surface 18 of the wall 16 is circular in section taken perpendicular to a longitudinal central axis or centerline 40 of the wall and the inner surface. The inner surface 18 has a substantially constant diameter from the proximal end 24 of the catheter 12 to the distal end 26. While shown as circular in cross-section, the inner surface 18 of the wall 16 may define any suitable closed geometric figure when viewed in cross-section taken transverse or, more particularly, perpendicular to its longitudinal centerline 40 and to the longitudinal extent of the wall.

The inner surface 18 of the wall 16 defines a central bore 22 that also extends substantially the entire length of the catheter 12. The central bore 22 is open at the distal end 26 of the catheter 12. In other words, the central bore 22 communicates with a port or opening 28 in the exterior surface or outer surface 20 of the catheter 12 at its distal end 26. The central bore 22 is also open at the opposite, proximal end 24 of the catheter 12. As it does at the distal end 26 of the catheter 12, the central bore 22 communicates with a port or opening 30 in a radially extending exterior surface 32 of the catheter at its proximal end 24. Because of the foregoing construction, unless the central bore 22 is closed or occluded, fluid or, more particularly, a liquid, may be introduced into the central bore 22 through the opening 30 in the proximal end 24 of the catheter 12, flow along the central bore 22, and then flow out the open distal end 26 of the catheter through the opening 28.

Within the central bore 22 of the catheter 12 is a divider or separator 14. The separator 14 shown in FIGS. 1-5 is a membrane 34 made of a flexible biocompatible material, such as a medical grade silicone. In other words, the material of which the membrane 34 is made is capable of being flexed, which is to say capable of being turned, bowed, or twisted without breaking. The membrane 34 may alternatively be made of a flexible and resilient biocompatible material, such as a medical grade silicone elastomer. In other words, the material of which the membrane 34 may alternatively be made is capable of both being flexed (flexible) and returning freely to a previous position, shape or condition, which is to say capable of recovering its size and shape after deformation (resilient).

Figure 1:
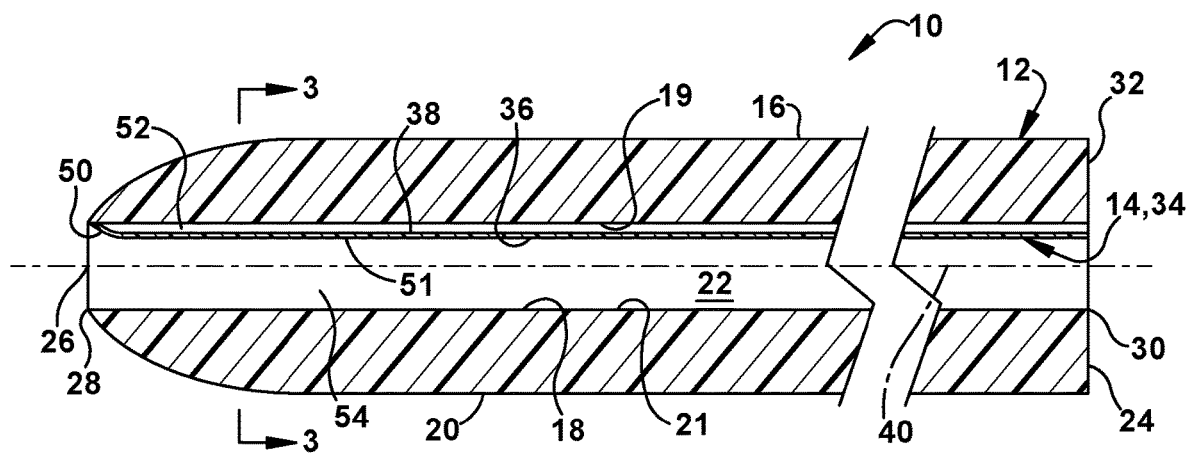
FIG. 1 is a sectional view of an embodiment of a catheter assembly in accordance with the present invention with an infusate lumen in an open or non-occluded condition.

The membrane 34 extends substantially the entire length of the central bore 22 from the proximal end 24 of the catheter 12 to the distal end 26 of the catheter. As can be seen in FIGS. 1 and 3, the membrane 34 includes a first major side surface 36, which is presented toward a lower portion 21 of the radially inner surface 18 of the catheter 12, as viewed in section taken perpendicular to the longitudinal centerline 40 of the inner surface 18 and the wall 16. The membrane 34 also includes a second major side surface 38, which is presented in a direction away from or opposite the first major side surface and toward an upper portion 19 of the radially inner surface 18 of the catheter 12, as viewed in section taken perpendicular to the longitudinal centerline 40 of the inner surface 18 and the wall 16. Both the first major side surface 36 and the second major side surface 38 extend substantially the entire length of the membrane 34.

Along the laterally opposite, longitudinally extending edges 42 and 44 of the first major side surface 36, and along the corresponding laterally opposite, longitudinally extending edges of the second major side surface 38, the membrane 34 is attached, joined, secured, or fixed directly to the inner surface 18 of the wall 16 of the catheter 12 so as to provide a fluid-tight seal against the passage of fluids, including both liquids and gases, such as air. As shown in FIG. 3, the laterally opposite, longitudinally extending edges 42 and 44 of the first major side surface 36 of the membrane 34 are sealingly attached, joined, secured, or fixed directly to the inner surface 18 of the wall 16 along diametrically opposite, attachment lines or narrow attachment surfaces 46 and 48 that extend longitudinally on the inner surface of the wall. The attachment, joining, securing, or fixing may accomplished by any suitable mechanism, such as co-molding the membrane 34 with the wall 16 of the catheter 12 or forming the membrane 34 separately from the wall 16 and attaching, joining, securing, or fixing the separately-formed membrane to the wall with a biocompatible adhesive.

Although the attachment surfaces 46 and 48 are shown in FIG. 3 as being at diametrically opposite locations on the inner surface 18 of the wall 16, the attachment surfaces may be at other locations. For example, the attachment surfaces 46 and 48 may be closer to each other along the upper portion 19 of the radially inner surface 18 of the catheter 12, as viewed in FIG. 3, so that the membrane 34 extends along a smaller portion of the radially inner surface 18 than is shown in FIG. 3. Alternatively, the attachment surfaces 46 and 48 may be closer to each other along the lower portion 21 of the radially inner surface 18 of the catheter 12, as viewed in FIG. 3, so that the membrane 34 extends along a greater portion of the radially inner surface 18 than is shown in FIG. 3. Regardless of the relative positions of the attachment surfaces 46 and 48, the membrane 34 extends loosely across the central bore 22 of the wall 16 of the catheter 12 and thus is disposed asymmetrically relative to the central bore 22 and relative to the closed geometric figure defined by the inner surface 18 surrounding the central bore when viewed in cross-section taken transverse or, more particularly, perpendicular to the longitudinal centerline 40 and the longitudinal extent of the wall.

Figure 2:
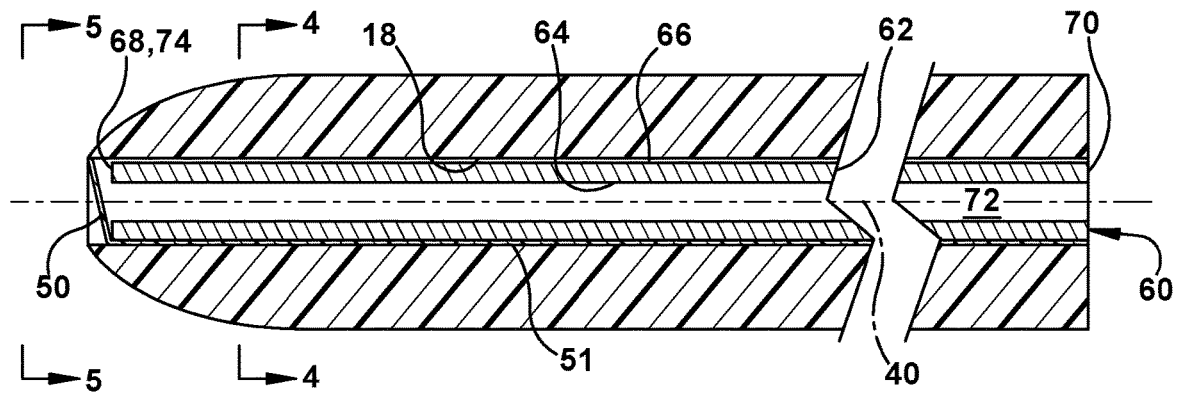
FIG. 2 is a sectional view the catheter assembly of FIG. 1 with the infusate lumen in a closed or occluded condition.

Adjacent the distal end 26 of the catheter 12, the membrane 34 extends laterally across the central bore 22 of the catheter so that a distal end portion 50 of the membrane closes off or occludes a portion of the central bore 22. To ensure a seal between the distal end portion 50 of the membrane 34 and the inner surface 18 of the wall 16, the attachment surfaces 46 and 48 extend toward each other and effectively merge at the top center of the inner surface 18, as viewed in FIG. 3. As best seen in FIG. 2, the distal end portion 50 of the membrane 34 comprises only a minor portion of the overall longitudinal extent of the membrane. A main portion 51 of the membrane 34 comprises a majority of the longitudinal extent of the membrane.

As a result of the longitudinal extent of the membrane 34 and the sealing attachment, joining, securing, or fixing between (a) the laterally opposite, longitudinally extending edges 42 and 44 of the first major side surface 36 of the membrane and (b) the inner surface 18 of the wall 16 of the catheter 12, the membrane 34 divides or separates the central bore 22 of the catheter into a stylet lumen or first lumen 52 and an infusate lumen or second lumen 54. Because the distal end portion 50 of the membrane 34 extends laterally across the central bore 22 of the catheter 12 and is sealingly attached, joined, secured, or fixed to the inner surface 18 of the wall 16, the distal end portion 50 closes off or occludes the distal end of the first lumen 52. The second lumen 54, on the other hand, remains open at both its distal end and its proximal end and communicates with the opening 28 at the distal end 26 of the catheter 12 and with the opening 30 at the proximal end 24 of the catheter. The first lumen 52 is thus effectively defined by the second major side surface 38 of the membrane 34 and the upper portion 19, as viewed in FIG. 3, of the inner surface 18 of the wall 16. Correspondingly, the second lumen 54 is effectively defined by the first major side surface 36 of the membrane 34 and the lower portion 21, as viewed in FIG. 3, of the inner surface 18 of the wall 16. The first lumen 52 and the second lumen 54 are laterally adjacent to one another or side-by-side in the central bore 22 of the catheter 12.

In use, the catheter assembly 10 includes a stylet 60, as shown in FIGS. 2 and 4. The stylet 60 is hollow and elongated and is formed of a relatively strong and rigid material, such as stainless steel. The stylet 60 includes a longitudinally extending tubular wall 62. The tubular wall 62 includes a radially inner surface 64 and a radially outer surface 66, which is presented in a direction away from or opposite the inner surface. Both the inner surface 64 and the outer surface 66 are circular in section taken perpendicular to the centerline 40 and to the length of the stylet 60 and extend substantially the entire length of the stylet 60 from a distal end 68 (best shown in FIG. 2) of the stylet to an opposite proximal end 70 of the stylet. The diameter of the inner surface 18 of the wall 16 of the catheter 12 and the diameter of the outer surface 66 of the wall 62 of the stylet 60 may be the same and typically would be substantially the same.

The inner surface 64 of the wall 62 defines a stylet lumen 72 that also extends substantially the entire length of the stylet 60. The stylet lumen 72 is open at the distal end 68 of the stylet 60 and at the opposite, proximal end 70 of the stylet. As a result of the foregoing construction, fluid, such as air, may flow along the stylet lumen 72 and then out the open distal end 68 of the stylet 60 or out the open proximal end 70.

The inner surface 64 of the wall 62 has a substantially constant diameter from the distal end 68 of the stylet 60 to the proximal end 70. The outer surface 66 of the stylet 60 also has a substantially constant diameter from the distal end 68 of the stylet 60 to the proximal end 70. A distal end outer surface 74 of the stylet 60 is oriented in a radial direction transverse or, more particularly, perpendicular to the length of the stylet. When the stylet 60 is inserted into the catheter 12, the radially extending distal end outer surface 74 is engageable with the distal end portion 50 of the membrane 34.

When the catheter assembly 10 is to be inserted into tissue, such as cerebral tissue, of a patient, the stylet 60 is inserted into the catheter 12. The stylet 60 is inserted into the central bore 22 of the catheter 12 and, specifically, into the stylet lumen or first lumen 52. The stylet 60 thus deflects or flexes the membrane 34 so that the membrane moves relative to the central bore 22. The membrane 34 moves from an undeflected or first position, which may be a position in which the main portion 51 of the membrane is adjacent the upper portion 19 of the inner surface 18 of the wall 16 of the catheter 12, as viewed in FIG. 3, to a deflected or second position in which the first major side surface 36 of the main portion 51 of the membrane is in close, sealing contact with the lower portion 21 of the inner surface 18 of the wall 16, as shown in FIG. 4. Although the undeflected or first position of the membrane 34 is shown in FIGS. 1 and 3 as being closely adjacent the upper portion 19 of the wall 16, which is convenient for purposes of illustrating the infusate lumen or second lumen 54, the undeflected or first position of the membrane may be any convenient position, such as a position adjacent the lower portion 21 of the wall 16. An undeflected or first position of the membrane 34 adjacent the lower portion 21 of the wall 16, as viewed in FIG. 3, may be desirable to facilitate insertion of the stylet 60. Such an undeflected or first position may be achieved either during the process of manufacturing the catheter 12 and the membrane 34 or as a result of manipulation of the membrane subsequent to manufacturing.

The stylet 60 is inserted into and pushed along the central bore 22 and the stylet lumen or first lumen 52 until the radially extending distal end outer surface 74 at the distal end 68 of the stylet contacts the distal end portion 50 of the membrane 34. The radially extending distal end outer surface 74 of the stylet 60 is thus positioned to transmit to the distal end portion 50 of the membrane 34 any pressure applied to the stylet. Pressure of the stylet 60 against the distal end portion 50 of the membrane 34 and a close fit between the outer surface 66 of the wall 62 of the stylet and the inner surface 18 of the wall 16 of the catheter 12 causes or permits the catheter 12 and the stylet to move more consistently as a single unit and to be manipulated more easily and accurately. In particular, the stylet 60 may be used to insert the catheter 12 into the tissue of a patient.

When the distal end 26 of the catheter 12 is appropriately positioned in a patient's tissue, the stylet 60 is withdrawn lengthwise from the catheter in a proximal direction. Because the distal end of the stylet lumen or first lumen 52 is closed by the distal end portion 50 of the membrane 34 and because the stylet 60 is hollow, air or other gas is not introduced into the patient's tissue. Rather, air may flow along the stylet lumen 72 to the distal end portion 50 of the membrane. The membrane 34 is also free, at locations distal of the distal end 68 of the stylet, as the stylet is being withdrawn, to return to its undeflected first position or to another position in which the first major side surface 36 of the main portion 51 of the membrane is spaced apart from or not sealingly engaged with the inner surface 18 of the wall 16 of the catheter 12.

With the catheter 12 of the catheter assembly 10 appropriately positioned in the patient's tissue, therapeutic treatment of the tissue with a bioactive material can begin. To introduce the bioactive material, a source of fluid, such as a liquid containing the bioactive material with which the patient's tissue is to be treated, is connected in fluid communication with the opening 30 at the proximal end 24 of the catheter 12 and thus with the central bore 22 and the infusate lumen or second lumen 54 of the catheter. Withdrawal of the stylet 60 from the central bore 22 of the catheter and introduction of the fluid into the second lumen 54 permits the fluid to flow through the second lumen and out of the opening 28 at the distal end 26 of the catheter and thereby be introduced into the patient's tissue. The pressure of the fluid flow helps to deflect the membrane 34 so that the second major side surface 38 of the membrane is closely adjacent the upper portion 19 of the inner surface 18 of the wall 16 of the catheter 12. When the patient's treatment is completed, the catheter assembly 10 may be withdrawn from the patient's tissue.

Figure 6:
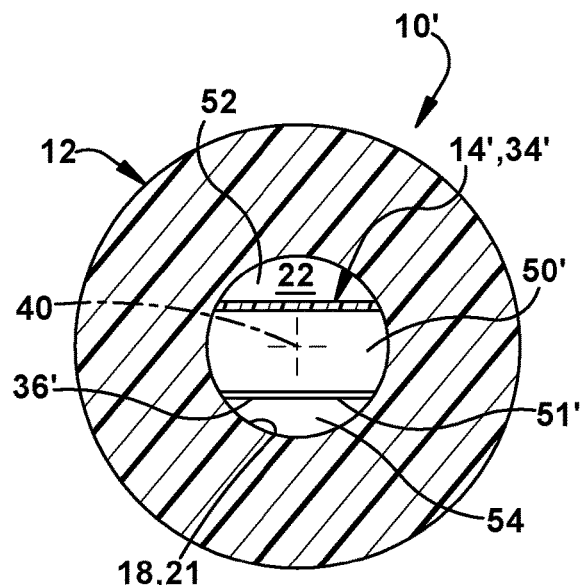
FIG. 6 is an enlarged transverse sectional view similar to FIG. 3 of a second embodiment of a catheter assembly in accordance with the present invention.

FIG. 6 illustrates a modified catheter assembly 10'. The construction of the modified catheter assembly 10' is substantially the same as the construction of the catheter assembly 10 of FIGS. 1-5, except the membrane 34' is formed of a flexible and resilient material, such as a biocompatible elastomer, rather than a material that is simply flexible. As can be seen in FIG. 6, which is a transverse sectional view of the catheter 12 taken at a location closer to the distal end 26 of the catheter and to the left of the view line 3-3 in FIG. 1, the main portion 51' of the membrane 34' is taut as it extends across the central bore 22 of the catheter, rather than loose like the main portion 51 of the membrane 34 shown in FIGS. 1 and 3.

The main portion 51' of the membrane 34' is also offset from the longitudinal centerline 40 of the wall 16 of the catheter 12 toward the lower portion 21 of the inner surface 18 of the wall of the catheter, as viewed in FIG. 6. Because the main portion 51' of the membrane 34' is offset from the centerline 40, the location of the membrane provides a visual cue at the proximal end 24 of the catheter 12 as to which lumen in the catheter is the stylet lumen or first lumen 52 and which lumen is the infusate lumen or second lumen 54. At the same time, because the membrane 34' is made of resilient material, the main portion 51' of the membrane can be flexed or deflected by the stylet 60 to a deflected position in which the first major side surface 36' of the main portion of the membrane is in close, sealing contact with the lower portion 21 of the inner surface 18 of the wall 16, similar to what is shown in FIG. 4. When the stylet 60 is removed from the catheter 12, the resilience of the material of which the membrane 34' is made cause the main portion 51' of the membrane to return to its undeflected or first position shown in FIG. 6.

As can be seen in FIG. 6, the main portion 51' of the membrane 34' is disposed asymmetrically relative to the central bore 22 of the wall 16 of the catheter 12 and relative to the closed geometric figure defined by the inner surface 18 surrounding the central bore when viewed in cross-section taken transverse or, more particularly, perpendicular to the longitudinal extent of the wall. In addition, as can be seen in FIG. 6, when the distal end portion 50' is viewed in section taken perpendicular to the longitudinal centerline 40, the distal end portion is also disposed asymmetrically relative to the central bore 22 of the wall 16 of the catheter 12 and relative to the closed geometric figure defined by the inner surface 18 surrounding the central bore. The foregoing asymmetric orientation is reflected by the position of the part of the distal end portion 50' shown in section in FIG. 6.

Figure 7:
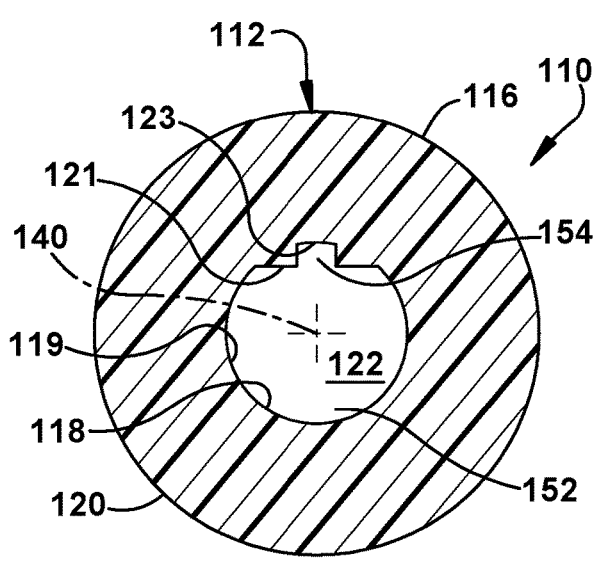
FIG. 7 is an enlarged transverse sectional view similar to FIG. 3 of a third embodiment of a catheter assembly in accordance with the present invention with a stylet lumen in an open or non-occluded condition.
Figure 8:
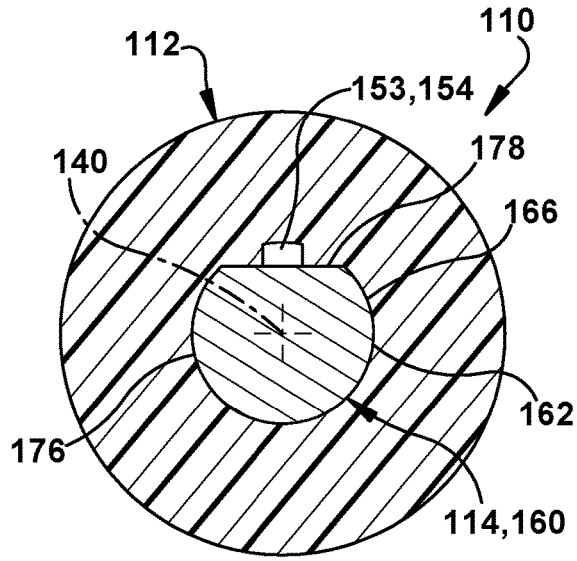
FIG. 8 is an enlarged transverse sectional view similar to FIG. 4 of the catheter assembly of FIG. 7 with the stylet lumen in a closed or occluded condition.

FIGS. 7 and 8 illustrate a catheter assembly 110 that is constructed in accordance with a second example of the present invention. The catheter assembly 110 includes a catheter 112. The catheter 112 is made of a flexible biocompatible material, such as a medical grade silicone. In other words, the material of which the catheter 112 is made is capable of being flexed, which is to say capable of being turned, bowed, or twisted without breaking. The catheter 112 may alternatively be made of a flexible and resilient biocompatible material, such as a medical grade silicone elastomer. In other words, the material of which the catheter 112 may alternatively be made is capable of returning freely to a previous position, shape or condition, which is to say capable of recovering its size and shape after deformation.

The catheter 112 includes a longitudinally extending, tubular wall 116. The wall 116 includes a radially inner surface 118 and a radially outer surface 120, which is presented in a direction away from or opposite the inner surface. Both the inner surface 118 and the outer surface 120 extend substantially the entire length of the catheter 112 from a distal end (not shown) of the catheter to an opposite proximal end (not shown) of the catheter.

As shown in FIGS. 7 and 8, a major circumferential portion 119 of the inner surface 118 of the wall 116, which is a lower portion of the wall as viewed in FIGS. 7 and 8, has the form of a circular arc in section taken perpendicular to a longitudinal central axis or centerline 140 of the wall and the inner surface. The inner surface 118 has a substantially constant diameter from the proximal end of the catheter 112 to the opposite distal end of the catheter. A minor circumferential portion 121 of the inner surface 118 of the wall 116, which is an upper portion of the wall as viewed in FIGS. 7 and 8, is flattened in section taken perpendicular to the axis or centerline 140, so as to resemble a chord of a circle, and has a squared notch 123 formed approximately midway across the minor circumferential portion 121. The cross-sectional shape of the minor circumferential portion 121 of the inner surface 118 of the wall 116 is substantially constant from the proximal end of the catheter 112 to the opposite distal end of the catheter. The inner surface 118 of the wall 116 may be configured as or may define any suitable closed geometric figure when viewed in cross-section taken transverse to the longitudinal axis or centerline 140 and to the longitudinal extent of the wall, provided that the squared notch 123 or another offset feature is included in the geometric figure.

The inner surface 118 of the wall 116 defines a central bore 122 that also extends substantially the entire length of the catheter 112. The central bore 122 is open at the distal end of the catheter 112. In other words, the central bore 122 communicates with a port or opening (not shown) in the exterior surface or outer surface 120 of the catheter 112 at its distal end (not shown). The central bore 122 is also open at the opposite, proximal end of the catheter 112. As it does at the distal end of the catheter 112, the central bore 122 communicates with a port or opening (not shown) in a radially extending exterior surface (not shown) of the catheter at its proximal end. Because of the foregoing construction, unless the central bore 122 is closed or occluded, fluid or, more particularly, a liquid, may be introduced into the central bore 122 through the opening in the proximal end of the catheter 112, flow along the central bore 122, and then flow out the open distal end of the catheter through the opening in the distal end.

In the catheter assembly 10 of FIGS. 1 through 5, a divider or separator 14 divides or separates the central bore 22 of the catheter into a stylet lumen or first lumen 52 and an infusate lumen or second lumen 54. In the catheter assembly 110 of FIGS. 7 and 8, the corresponding divider or separator 114 is a stylet 160. The stylet 160 is solid and elongated and is formed of a relatively strong and rigid material, such as stainless steel. The stylet 160 includes a longitudinally extending body 162. The body 162 includes a radially outer peripheral surface 166, which extends substantially the entire length of the stylet 160 from a distal end (not shown) of the stylet to an opposite proximal end (not shown) of the stylet. The diameter of the inner surface 118 of the wall 116 of the catheter 112 and the diameter of the outer peripheral surface 166 of the stylet 60 may be the same and typically would be substantially the same.

The outer peripheral surface 166 of the stylet 160 has a shape, when viewed in transverse section or section taken perpendicular to the axis or centerline 140, that is similar, but not identical to the cross-sectional shape of the inner surface 118 of the wall 116 of the catheter 112. More particularly, the cross-sectional shape of the outer peripheral surface 166 of the stylet 160 taken transverse or perpendicular to the axis or centerline 140 and to the longitudinal extent of the outer surface includes a major circumferential portion 176, which is a lower portion of the outer surface as viewed in FIG. 8, is a portion of a circle and has a substantially constant diameter from the proximal end of the stylet to the opposite distal end of the stylet. A minor circumferential portion 178 of the outer peripheral surface 166 of the stylet 160, which is an upper portion of the outer surface as viewed in FIG. 8, is flat in section taken perpendicular to the axis or centerline 140, like a chord of a circle. The cross-sectional shape of the minor circumferential portion 178 of the outer peripheral surface 166 of the stylet 160 is substantially constant from the proximal end of the stylet to the opposite distal end of the stylet.

The inner peripheral dimensions of the inner surface 118 of the wall 116 of the catheter 112 and the outer peripheral dimensions of the outer peripheral surface 166 of the body 162 of the stylet 160 may be the same and typically would be substantially the same, except for the notch 123 in the inner surface of the wall of the catheter. The outer peripheral surface 166 of the body 162 of the stylet 160 may define any suitable closed geometric figure when viewed in cross-section taken transverse to the axis or centerline 140 and to the longitudinal extent of the wall, provided that the squared notch 123 or other offset feature included in the inner surface 118 of the wall 116 is not included in the outer peripheral surface of the body of the stylet.

As can be seen in FIG. 8, when the stylet 160 is inserted into the central bore 122 of the catheter 112, the difference between the cross-sectional shape of the minor circumferential portion 178 of the outer peripheral surface 166 of the stylet and the cross-sectional shape of the minor circumferential portion 121 of the inner surface 118 of the wall 116 of the catheter 112 results in an open space 153 within the notch 123 of the minor circumferential portion of the inner surface of the wall of the catheter. The open space 153 extends for substantially the entire length of the portion of the stylet 160 received in the central bore 122 of the catheter 112. The result is that the open space 153 is a lumen 154 through which infusate may flow while the stylet is disposed in the central bore 122. The infusate lumen or second lumen 154 is thus defined by the notch 123 in the minor circumferential portion 121 of the inner surface 118 and the adjacent part of the minor circumferential portion 178 of the outer peripheral surface 166 of the body 162 of the stylet 160. The infusate lumen 154 is open at both its distal end and its proximal end and communicates with the opening at the distal end of the catheter 112 and with the opening at the proximal end of the catheter. When the stylet 160 is removed from the central bore 122, the infusate lumen 154 is no longer a separate flow path for infusate, but rather communicates throughout its length with a stylet lumen or first lumen 152 within the central bore 122, which is the portion of the central bore that receives the stylet, as shown in FIG. 8.

When the catheter assembly 110 is to be inserted into tissue, such as cerebral tissue, of a patient, the stylet 160 is inserted into the catheter 112. The stylet 160 is inserted into the central bore 122 of the catheter 112 and, specifically, into the stylet lumen or first lumen 152. The stylet 160 thus defines and separates or divides the infusate lumen or second lumen 154 from the stylet lumen or first lumen 152. The major circumferential portion 176 of the outer peripheral surface 166 of the stylet 160 is in close, sealing contact with the major circumferential portion 119 of the inner surface 118 of the wall 116, as shown in FIG. 8. The close fit between the major circumferential portion 176 of the outer peripheral surface 166 of the body 162 of the stylet 160 and the major circumferential portion 119 of the inner surface 118 of the wall 116 of the catheter 112 closes or occludes the first lumen 152 and causes or permits the catheter and the stylet to move more consistently as a single unit and to be manipulated more easily and accurately. In particular, the stylet 160 may be used to insert the catheter 112 into the tissue of a patient.

When the distal end of the catheter 112 is appropriately positioned in a patient's tissue, the stylet 160 may be withdrawn lengthwise from the catheter in a proximal direction. Before the stylet is withdrawn, however, liquid is introduced into the proximal end of the infusate lumen 154 so as to fill the infusate lumen from its proximal end to its distal end. The liquid may be a liquid containing a bioactive material with which the patient's tissue is to be treated. To ensure that the infusate lumen 154 remains filled with the liquid, a source of liquid is connected in fluid communication with the open proximal end (not shown) of the catheter 112 and thus with the central bore 122 and the infusate or second lumen 154 of the catheter 112. As the stylet 160 is withdrawn from the first lumen 152 of the catheter 112, the movement of the stylet creates a vacuum within the central bore 122, which, in turn, draws the liquid into the first lumen from the second lumen 154 and, ultimately, the source of liquid. The introduction of the liquid into the infusate lumen 154 and the subsequent withdrawal of the stylet 160 from the central bore 122 of the catheter provides a "self-priming" action by which the proximal movement of the distal end of the stylet draws the fluid into the distal end portion of the central bore 122 to restrict or prevent air or other gas from being drawn into the catheter and introduced into the patient's tissue.

With the catheter 12 of the catheter assembly 10 appropriately positioned in the patient's tissue and the stylet 160 withdrawn, therapeutic treatment of the tissue with the bioactive material can begin. To introduce the bioactive material, a source of fluid, such as a liquid containing the bioactive material with which the patient's tissue is to be treated, is connected in fluid communication with the open proximal end of the catheter and thus with the central bore 122 and both the infusate lumen or second lumen 154 and the stylet lumen or first lumen 152 of the catheter 112. The liquid is free to flow through the central bore 122 and both the infusate or second lumen 154 and the stylet lumen or first lumen 152 of the catheter 112 and out of the opening at the distal end of the catheter and into the patient's tissue. When the patient's treatment is completed, the catheter assembly 110 may be withdrawn from the patient's tissue.

To facilitate insertion of the stylet 160 into the central bore 122 of the catheter 112, the proximal end (not shown) of the catheter may be attached or fixed to a cap that is dimensioned and configured to guide the stylet into the catheter and that also incorporates a fill tube or fluid line for delivering liquid to the infusate lumen 154. After the stylet 160 is removed from the catheter 112 and the central bore 122 of the catheter is filled with liquid, the cap may be removed by cutting the catheter along a marked or weaken line or narrow area circumscribing the catheter adjacent the cap and the proximal end of the catheter. A pressure fit adapter may then be attached to the newly cut proximal end of the catheter 112 to connect the catheter to tubing through which the liquid containing the bioactive material may be delivered to the catheter.

While the catheters 12 and 112 are described as being formed of either a flexible biocompatible material or a flexible and resilient biocompatible material, the use of a resilient biocompatible material will facilitate the use of a stylet to extend the catheters 12 and 112 longitudinally and reduce their diameters upon insertion into a patient's tissue and then to allow the catheters to return to their initial lengths and diameters, as described in U. S. Patent Application Publication US 2012/0323175. Also, while the catheters 12 and 112 have been described as being introduced into a patient's tissue and then later removed from the patient's tissue, the catheters may be fabricated of a material or materials that can be absorbed by the tissue, thereby reducing or eliminating the requirement physically to remove the catheters from the patient's tissue.

It will be appreciated that the catheter assemblies 10, 10', and 110 may be used to treat both neoplastic and non-neoplastic disorders. Bioactive materials introduced into a patient's tissue using any of the catheter assemblies 10, 10', and 110 may include, for example, chemotherapeutic materials, viruses, proteins, radiologic materials, growth factors, peptides, and non-radioactive tracer molecules. The catheter assemblies 10, 10', and 110 may be used in a variety of patient tissues, including, for example, brain tissue, spinal cord tissue, and tissue of any organ.

From the above description of the invention, those skilled in the art will perceive improvements, changes and modifications. Such improvements, changes, and/or modifications within the skill of the art are intended to be covered by the appended claims.

Having described the invention, the following is claimed:

1. A catheter assembly comprising:
   a stylet having an open distal end and an open proximal end,
   a catheter including a longitudinally extending wall with an inner surface and an outer surface, the inner surface of the wall (a) defining a bore having a longitudinal axis and extending longitudinally through the catheter and (b) at least partially defining a first lumen in the bore sized and configured to receive the stylet and a laterally adjacent second lumen in the bore sized and configured to receive an infusate, at least one of the first lumen and the second lumen communicating with an opening in the outer surface of the wall adjacent a distal end of the catheter, and
   an elongated separator including a longitudinally extending surface that at least partially defines the second lumen, the longitudinally extending surface of the separator being disposed asymmetrically relative to the longitudinal axis of the bore when viewed in cross-section taken transverse to a longitudinal extent of the separator adjacent to a distal end of the separator, at least a portion of the separator being movable relative to the bore and the inner surface of the wall of the catheter.

2. A catheter assembly according to claim 1 wherein the separator includes a flexible membrane extending longitudinally through the bore, the membrane including a first major side surface presented toward the second lumen and an opposite second major side surface presented toward the first lumen, the membrane being attached to the wall of the catheter adjacent opposed edges of the first major side surface throughout a majority of the longitudinal extent of the membrane so as to separate the bore into the first lumen and the second lumen, the membrane extending transversely of the bore and being attached to the wall along a distal end portion of the membrane so as to close a distal end of the first lumen, at least a portion of the membrane being movable relative to the bore and the inner surface of the wall of the catheter.

3. A catheter assembly according to claim 2 wherein the membrane is sealingly directly attached to the wall of the catheter.

4. A catheter assembly according to claim 2 wherein the stylet is a hollow stylet, the stylet being receivable in the first lumen and being configured and dimensioned to cause the portion of the membrane to move laterally relative to the bore and the inner surface of the wall to occlude the second lumen.

5. A catheter assembly according to claim 4 wherein the stylet has a length and an outer surface, the outer surface of the stylet including a portion oriented in a radial direction transverse to the length of the stylet, the portion of the outer surface of the stylet being positionable to transmit pressure to the membrane at a location where the membrane extends transversely across the bore so as to close the distal end of the first lumen.

6. A method for performing a medical procedure using the catheter assembly of claim 1 comprising the steps of:
   (a) placing the stylet in the bore of the catheter;
   (b) disposing the catheter, together with the stylet placed in the bore of the stylet, in tissue of a patient so that the distal end of the catheter is positioned at a desired location in the tissue; and
   (c) after the distal end of the catheter is positioned at a desired location in the tissue, removing the stylet from the bore of the catheter and introducing a fluid containing a bioactive material into the second lumen of the catheter so that the fluid flows through at least the second lumen into the tissue.

7. A method according to claim 6 wherein the separator of the catheter assembly includes a flexible membrane extending longitudinally through the bore, the membrane including a first major side surface presented toward the first lumen and an opposite second major side surface presented toward the second lumen, the membrane being attached to the wall of the catheter adjacent opposed edges of the first major side surface throughout a majority of the longitudinal extent of the membrane so as to separate the bore into the first lumen and the second lumen, the membrane extending transversely of the bore and being attached to the wall along a distal end portion of the membrane so as to close a distal end of the first lumen, at least a portion of the membrane being movable relative to the bore and the inner surface of the wall of the catheter.

8. A method according to claim 7 wherein the membrane is sealingly directly attached to the wall of the catheter.

9. A method according to claim 7 in which the stylet is hollow, the stylet being receivable in the first lumen and being configured and dimensioned to cause the portion of the membrane to move laterally relative to the bore and the inner surface of the wall to occlude the second lumen.

10. A catheter assembly comprising:
a stylet having an open distal end and an open proximal end,
a catheter including a longitudinally extending wall with an inner surface and an outer surface, the inner surface of the wall (a) defining a bore having a longitudinal axis and extending longitudinally through the catheter and (b) at least partially defining a first lumen in the bore sized and configured to receive the stylet and a laterally adjacent second lumen in the bore sized and configured to receive an infusate, the second lumen communicating with an opening in the outer surface of the wall adjacent a distal end of the catheter, and
a flexible membrane extending longitudinally through the bore, the membrane including a first major side surface presented toward the second lumen and an opposite second major side surface present toward the first lumen, the membrane being attached to the wall of the catheter adjacent opposed edges of the first major side surface throughout a majority of a longitudinal extent of the membrane so as to separate the bore into the first lumen and the second lumen, the membrane extending transversely of the bore and being attached to the wall along a distal portion of the membrane so as to close a distal end of the first lumen, at least a portion of the membrane being movable relative to the bore and the inner surface of the wall of the catheter.

11. A catheter assembly according to claim 10 wherein the stylet is a hollow stylet, the stylet being receivable in the first lumen and being configured and dimensioned to cause the portion of the membrane to move laterally relative to the bore and the inner surface of the wall to occlude the second lumen.

12. A catheter assembly according to claim 11 wherein the stylet has a length and an outer surface, the outer surface of the stylet including a portion oriented in a radial direction transverse to the length of the stylet, the portion of the outer surface of the stylet being positionable to transmit pressure to the membrane at a location where the membrane extends transversely across the bore so as to close the distal end of the first lumen.

13. A catheter assembly according to claim 10 wherein the membrane is sealingly directly attached to the wall of the catheter.

* * * * *